United States Patent
Yoshino et al.

(10) Patent No.: US 11,154,534 B2
(45) Date of Patent: Oct. 26, 2021

(54) LIPID PARTICLE COMPOSITION AND PHARMACEUTICAL COMPOSITION

(71) Applicant: FUJIFILM Corporation, Tokyo (JP)

(72) Inventors: Yuta Yoshino, Ashigarakami-gun (JP); Hayato Ogura, Ashigarakami-gun (JP); Mikinaga Mori, Ashigarakami-gun (JP); Taisuke Endo, Ashigarakami-gun (JP); Kentaro Numajiri, Ashigarakami-gun (JP); Ritsuko Hori, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/448,069

(22) Filed: Jun. 21, 2019

(65) Prior Publication Data
US 2019/0314335 A1 Oct. 17, 2019

Related U.S. Application Data

(63) Continuation of application No. PCT/JP2017/046564, filed on Dec. 26, 2017.

(30) Foreign Application Priority Data

Dec. 26, 2016 (JP) .............................. JP2016-250826

(51) Int. Cl.
A61K 31/4045 (2006.01)
A61K 9/127 (2006.01)
A61K 35/00 (2006.01)

(52) U.S. Cl.
CPC .......... *A61K 31/4045* (2013.01); *A61K 9/127* (2013.01); *A61K 35/00* (2013.01)

(58) Field of Classification Search
None
See application file for complete search history.

(56) References Cited

U.S. PATENT DOCUMENTS

| | | | |
|---|---|---|---|
| 9,603,800 B2 * | 3/2017 | Fahmy | A61K 38/2013 |
| 10,507,182 B2 | 12/2019 | Hayes et al. | |
| 2003/0147945 A1 * | 8/2003 | Tardi | A61K 31/7068 424/450 |
| 2015/0209282 A1 | 7/2015 | Chu et al. | |
| 2016/0324780 A1 * | 11/2016 | Hayes | B01J 13/08 |
| 2019/0151468 A1 | 5/2019 | Coulter et al. | |

FOREIGN PATENT DOCUMENTS

| | | |
|---|---|---|
| CN | 105163720 A | 12/2015 |
| JP | 2019-513139 A | 5/2019 |
| WO | 2014/121211 A2 | 8/2014 |
| WO | 2016/022549 A1 | 2/2016 |
| WO | 2016/191363 A1 | 12/2016 |
| WO | 2017/167837 A1 | 10/2017 |

OTHER PUBLICATIONS

Crisanti et al (Mol Cancer Ther, 2009, 8(8), 2221-2231). (Year: 2009).*
Maiso et al (Leukemia, 2009, 23, 2265-2274). (Year: 2009).*
Keitaro Sou et al., "Bone marrow-targeted liposomal carriers", Expert Opin. Drug Deliv., 2011, vol. 8, No. 3, pp. 317-328 (12 pages total).
Abstract #5534: "Liposome accumulation within leukemia engrafted bone marrow is significantly enhanced when the formulation contains cytarabine plus daunorubicin", Sharon A. Johnstone, Sherwin Xie, Troy Harasym, Lawrence Mayer and Paul G. Tardi, DOI: 10.1158/1538-7445. AM10-5534 Published Apr. 15, 2010: AACR 101st Annual Meeting 2010, Proceedings, vol. 51, Apr. 17-21, 2010; Washington, DC, 8 pages total.
Fukaya, Natsuki et al., "Development and Cancer Treatment Applications of Histone Deacetylation Enzyme Inhibitor-Containing Ribosomes", Abstracts of the 136th Annual Meeting of the Pharmaceutical Society of Japan: 4, Mar. 2016, p. 68 (28N-pm06S) (3 pages total) (non-official translation).
Package Insert, "Farydak (R) capsules", 1st Edition, 2015, pp. 1-8 (8 pages total).
Antonia K et al., "Polycomb Target Genes Are Silenced in Multiple Myeloma", PLoS ONE, Jul. 2010, vol. 5, Issue 7, e11483, pp. 1-12 (12 pages total).
Chen, H. et al., "Development of Histone Deacetylation Enzyme Inhibitor-Containing Ribosomes for Cancer Treatment Purposes", Abstracts of the 137th Annual Meeting of the Pharmaceutical Society of Japan: 4, Mar. 5, 2017, p. 91 (27I-pm11S) (3 pages total) (non-official translation).
International Searching Report dated Feb. 13, 2018, issued by the International Searching Authority in application No. PCT/JP2017/046564.
Written Opinion dated Feb. 13, 2018, issued by the International Searching Authority in application No. PCT/JP2017/046564.
International Preliminary Report on Patentability dated Jul. 2, 2019, issued by the International Bureau in application No. PCT/JP2017/046564.
Sharon A. Johnstone et al., "Abstract 5534: Liposome accumulation within leukemia engrafted bone marrow is significantly enhanced when the formulation contains cytarabine plus daunorubicin", Cancer Research, vol. 70, Issue 8 Supplement, Apr. 2010 (4 pages total).
Extended European Search Report dated May 20, 2020 in European Application No. 17888488.8.
Fukaya et al., "Application for the development and treatment of histone deacetylase", Pharmaceutical Society of Japan, one hundred thirty sixth Summary, Mar. 2016, p. 68, (28N-pm06 S), 4 pages total.

(Continued)

*Primary Examiner* — Celeste A Roney
(74) *Attorney, Agent, or Firm* — Sughrue Mion, PLLC

(57) ABSTRACT

An object of the present invention is to provide a lipid particle composition containing panobinostat or a salt thereof and exhibiting a high bone marrow-targeting capability, and a pharmaceutical composition including the lipid particle composition. According to the present invention, provided is a lipid particle composition containing panobinostat or a salt thereof, in which a lipid particle contains a phospholipid and cholesterol.

15 Claims, 6 Drawing Sheets

(56) References Cited

OTHER PUBLICATIONS

A package insert "Farydak ® capsules", NOVARTIS, 2015, the 1st edition, pp. 1-8, 9 pages total.
Kalushkova et al., "Polycomb Target Genes Are Silenced in Multiple Myeloma", PLoS ONE, Jul. 2010, vol. 5, Issue 7, e11483, pp. 1-12, 13 pages total.
Office Action dated Apr. 28, 2020, from the Japanese Patent Office in JP Application No. 2018-559499.
Keitaro Sou et al., "Selective uptake of surface-modified phospholipid vesicles by bone marrow macrophages in vivo", Biomaterials, vol. 28, 2007, pp. 2655-2666 (13 pages total).
Keitaro Sou et al., "Bone marrow-targeted liposomal carriers", Expert Opin. Drug Deliv., 2011, vol. 8, No. 3, pp. 317-328 (19 pages total).
Office Action dated Nov. 10, 2020 from the Japanese Patent Office in JP Application No. 2018-559499.
Office Action issued in Chinese Patent Application No. 201780080668.3 dated Aug. 17, 2021; 23 pages.

\* cited by examiner

LIPID PARTICLE COMPOSITION AND PHARMACEUTICAL COMPOSITION

CROSS-REFERENCE TO RELATED APPLICATIONS

This application is a Continuation of PCT International Application No. PCT/JP2017/046564 filed on Dec. 26, 2017, which claims priority under 35 U.S.C § 119(a) to Japanese Patent Application No. 2016-250826 filed on Dec. 26, 2016. Each of the above application(s) is hereby expressly incorporated by reference, in its entirety, into the present application.

BACKGROUND OF THE INVENTION

1. Field of the Invention

The present invention relates to a lipid particle composition containing panobinostat or a salt thereof, and a pharmaceutical composition including the lipid particle composition.

2. Description of the Related Art

Panobinostat is a hydroxamic acid derivative used for the treatment of multiple myeloma and is one of non-selective histone deacetylase inhibitors. Panobinostat is commercially available in the form of a capsule-type oral preparation under a trade name of FARYDAK (registered trademark).

On the other hand, it is often studied that a drug is accumulated in cancer and exposed over a long period of time by means of a liposome preparation. The liposome preparation is a preparation in which a drug is encapsulated in a liposome constituted of a lipid membrane.

For example, literature [Keitaro Sou et al., Expert Opin Drug Deliv. 2011 March; 8(3): 317-328] discloses a liposome preparation targeting the bone marrow. Literature [Keitaro Sou et al., Expert Opin Drug Deliv. 2011 March; 8(3): 317-328] discloses a liposome containing 1,2-dipalmitoyl-sn-glycero-3-phosphocholine (DPPC), cholesterol, L-glutamic acid, N-(3-carboxyl-1-oxopropyl)-1,5-dihexadecyl ester (SA lipid), and poly(ethylene glycol) and discloses that the SA lipid component is an active factor inducing phagocytosis by myeloid phagocytes.

Literature [Abstract 5534: Liposome accumulation within leukemia engrafted bone marrow is significantly enhanced when the formulation contains cytarabine plus daunorubicin, Sharon A. Johnstone, Sherwin Xie, Troy Harasym, Lawrence Mayer and Paul G. Tardi, DOI: 10.1158/1538-7445.AM10-5534 Published 15 Apr. 2010, Proceedings: AACR 101st Annual Meeting 2010, Apr. 17-21, 2010; Washington, D.C.] discloses that a liposome (CPX-351) encapsulating cytarabine and daunorubicin exhibits high bone marrow accumulation properties. Literature [Abstract 5534: Liposome accumulation within leukemia engrafted bone marrow is significantly enhanced when the formulation contains cytarabine plus daunorubicin, Sharon A. Johnstone, Sherwin Xie, Troy Harasym, Lawrence Mayer and Paul G. Tardi, DOI: 10.1158/1538-7445.AM10-5534 Published 15 Apr. 2010, Proceedings: AACR 101st Annual Meeting 2010, Apr. 17-21, 2010; Washington, D.C.] discloses that accumulation of CPX-351 in the bone marrow is 20% to 50% higher in a normal mouse as compared to an empty liposome, and 75% higher in a leukemia model mouse as compared to an empty liposome.

SUMMARY OF THE INVENTION

As mentioned above, although there have been some reports of liposomes exhibiting high bone marrow accumulation properties, there is no finding of liposome compositions containing panobinostat or a salt thereof and exhibiting a high bone marrow-targeting capability. An object of the present invention is to provide a lipid particle composition containing panobinostat or a salt thereof and exhibiting a high bone marrow-targeting capability, and a pharmaceutical composition including the lipid particle composition.

As a result of extensive investigations in order to achieve the foregoing object, the present inventors have found that a lipid particle composition containing panobinostat or a salt thereof, in which the lipid particles contain a phospholipid and cholesterol, exhibits a high bone marrow-targeting capability. The present invention has been completed based on these findings.

That is, the present invention provides the following.

[1] A lipid particle composition comprising:
panobinostat or a salt thereof,
in which a lipid particle contains a phospholipid and cholesterol.

[2] A lipid particle composition comprising:
panobinostat or a salt thereof,
in which an area ratio represented by Formula 1 up to infinite time after single administration of a lipid particle composition of 4 mg/kg as a panobinostat amount to a tail vein of a mouse is 5 or more.

Formula 1: (area under bone marrow concentration-time curve)/(area under gastrointestinal tract concentration-time curve)

[3] The lipid particle composition according to [1] or [2], in which the lipid particle has an average particle size of 50 nm to 500 nm.

[4] The lipid particle composition according to any one of [1] to [3], in which the panobinostat or the salt thereof is encapsulated in the lipid particle by a remote loading method.

[5] The lipid particle composition according to any one of [1] to [4], in which a solidified material of the panobinostat or the salt thereof is present in at least a part of a surface and an inside of the lipid particle.

[6] The lipid particle composition according to any one of [2] to [5], in which the lipid particle contains a phospholipid and cholesterol.

[7] The lipid particle composition according to any one of [1] to [6], which contains a phospholipid having a glycerol skeleton, as the phospholipid.

[8] The lipid particle composition according to [7], in which the phospholipid having a glycerol skeleton is phosphatidylcholine.

[9] The lipid particle composition according to any one of [1] to [6], which contains a sphingophospholipid as the phospholipid.

[10] The lipid particle composition according to [9], in which the sphingophospholipid is sphingomyelin.

[11] The lipid particle composition according to any one of [1] to [10], in which the phospholipid contains a fatty acid residue having 20 or more carbon atoms.

[12] The lipid particle composition according to any one of [1] to [11], in which the lipid particle further contains a polyethylene glycol lipid.

[13] The lipid particle composition according to [12], in which a percentage of the polyethylene glycol lipid in total lipids constituting the lipid particle is 5 mol % or less.

[14] The lipid particle composition according to any one of [1] to [11], in which the lipid particle is substantially free of a polyethylene glycol lipid.

[15] The lipid particle composition according to any one of [1] to [14], in which the lipid particle contains an anionic lipid.

[16] A pharmaceutical composition comprising:
the lipid particle composition according to any one of [1] to [15].

[17] The pharmaceutical composition according to [16], which is an anticancer agent.

[18] A method for treating a subject, comprising:
administering the lipid particle composition according to any one of [1] to [17] to a subject.

[19] The lipid particle composition according to any one of [1] to [17] for use in the treatment of cancer.

[20] Use of the lipid particle composition according to any one of [1] to [17] for the production of a pharmaceutical composition.

[21] Use of the lipid particle composition according to any one of [1] to [17] for the production of an anticancer agent.

The lipid particle composition and pharmaceutical composition of the present invention exhibit a high bone marrow-targeting capability. According to the lipid particle composition and the pharmaceutical composition of the present invention, a pharmaceutical composition having an improved therapeutic index can be provided.

DESCRIPTION OF THE PREFERRED EMBODIMENTS

Figure 1:
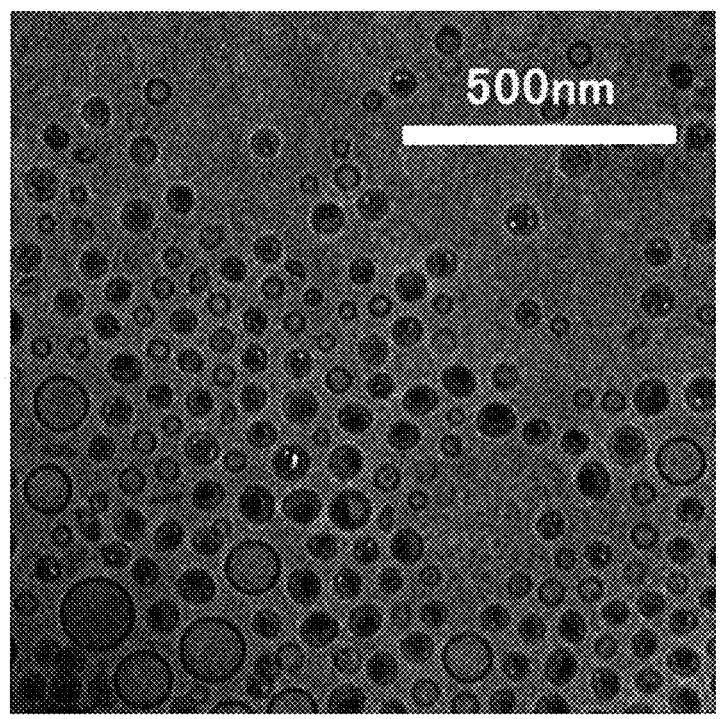
FIG. 1 shows a transmission electron microscope (TEM) image of a panobinostat-containing lipid particle.

The numerical range indicated by using "to" in the present specification means a range including the numerical values described before and after "to" as the minimum value and the maximum value, respectively.

In referring herein to a content of a component in a composition, in a case where plural substances exist corresponding to a component in the composition, the content means, unless otherwise specified, the total amount of the plural substances existing in the composition.

The term "empty liposome" means a liposome that does not contain a drug.

The term "release" means that a drug contained in a lipid particle (liposome or the like) passes through a lipid membrane constituting the lipid particle (liposome or the like) and then goes out of the lipid particle (liposome or the like).

The term "retentivity in blood" means a property in which a drug in a state of being encapsulated in a lipid particle (liposome or the like) is present in blood in a subject to which a lipid particle (liposome or the like) composition has been administered.

The term "average particle size of the lipid particle (liposome or the like)" means a volume average particle size of the lipid particle (liposome or the like) present in the lipid particle (liposome or the like) composition. The average particle size of the lipid particle contained in the lipid particle composition according to the embodiment of the present invention is measured using a dynamic light scattering method. Examples of commercially available measurement devices using dynamic light scattering include a concentrated system particle size analyzer FPAR-1000 (manufactured by Otsuka Electronics Co., Ltd.), a NANO-TRAC UPA (manufactured by Nikkiso Co., Ltd.), and a NANOSIZER (manufactured by Malvern Panalytical Ltd.).

The "subject" is a mammal such as a human, a mouse, a monkey, or a domestic animal in need of the prevention or treatment of a disease or the like, and preferably a human in need of the prevention or treatment of a disease or the like.

Hereinafter, the present invention will be described in detail.

The lipid particle composition according to the embodiment of the present invention is a lipid particle composition containing panobinostat or a salt thereof, in which the lipid particle contains a phospholipid and cholesterol.

(Lipid Particle)

A lipid particle means a particle constituted of a lipid and is not particularly limited. The lipid particle of the present invention includes a liposome having a lamellar structure which is a closed vesicular body constituted of a bimolecular lipid membrane. The liposome is a closed vesicular body formed of a lipid bilayer membrane using lipids, and has a water phase (inner water phase) within the space of the closed vesicle. The inner water phase contains water and the like. The liposome is usually present in a state of being dispersed in an aqueous solution (outer water phase) outside the closed vesicle. The liposome may be single lamellar (which is also referred to as monolayer lamellar or unilamellar, and is a structure having a single bilayer membrane) or multilayered lamellar (which is also referred to as multilamellar and is an onion-like structure having multiple bilayer membranes where individual layers are compartmented by aqueous layers). In the present invention, a single lamellar liposome is preferred from the viewpoint of safety and stability in pharmaceutical applications.

The lipid particle of the present invention also includes a particle which does not have the bimolecular lipid membrane structure (lamellar structure) of the above-described liposome and has a structure in which the inside of the particle is also filled with constituent components.

The form of the lipid formation can be confirmed by electron microscopic observation, structure analysis using X-rays, or the like. For example, it is possible to confirm that a lipid particle has a structure having a bimolecular lipid membrane structure (lamellar structure) and an inner water layer like a liposome, or a structure which does not have a bimolecular lipid membrane structure (lamellar structure) and an inner water layer unlike a liposome and has a core with a high electron density in the inside of the particle, thus resulting in a structure filled with constituent components including lipids, by means of a method in which cryo-transmission electron microscopy observation (CryoTEM method) is used. It is also possible to confirm the presence and absence of the bimolecular lipid membrane structure (lamellar structure) in a lipid particle even through X-ray small angle scattering (SAXS) measurement.

The lipid particle is not particularly limited in terms of form thereof as long as it is a lipid particle capable of encapsulating a drug. The "encapsulating" means taking a form in which a drug is contained in an inner water phase and/or a membrane itself with respect to the lipid particle. For example, the liposome may be a form where a drug is encapsulated within a closed space formed of a membrane, a form where a drug is encapsulated in the membrane itself, or a combination thereof.

The average particle size of the lipid particle is generally 10 nm to 1000 nm, preferably 50 nm to 500 nm, more preferably 100 nm to 500 nm, and still more preferably 100 nm to 300 nm.

The lipid particle is preferably in the form of a spherical shape or a morphology close thereto.

The zeta potential of the lipid particle according to the present invention is not particularly limited, but it is preferably −10 mV or less, more preferably −15 mV or less, and still more preferably −20 mV or less. The zeta potential of the lipid particle is also preferably −25 mV or less and more preferably −30 mV or less.

The component constituting the lipid bilayer of a lipid particle is selected from lipids. As the lipid, any one may be used as long as it is dissolved in a mixed solvent of a water-soluble organic solvent and an ester-based organic solvent. Examples of lipids include phospholipids, lipids other than phospholipids, cholesterols, lysophospholipids, and derivatives thereof. These components may be composed of single or plural components. The lipid particles in the present invention contain at least phospholipids and cholesterols.

Examples of the phospholipid include natural or synthetic phospholipids such as phosphatidylcholine (lecithin), phosphatidyl glycerol, phosphatidic acid, phosphatidyl ethanolamine, phosphatidyl serine, phosphatidyl inositol, sphingomyelin, dihydrosphingomyelin, and cardiolipin, and hydrogenated products thereof (for example, hydrogenated soybean phosphatidylcholine (HSPC)). In the present invention, the term "phospholipid" also encompasses a phospholipid derivative in which the phospholipid is modified.

In the present invention, the phospholipid preferably includes a phospholipid having a glycerol skeleton. The phospholipid having a glycerol skeleton is particularly preferably phosphatidylcholine. 1,2-diarachidonoyl-sn-glycero-3-phosphocholine or the like can be used as the phosphatidylcholine. In the present invention, it is also preferable to include sphingophospholipid as the phospholipid. Sphingomyelin or the like can be used as sphingophospholipid.

The phospholipid in the present invention preferably contains a fatty acid residue having 20 or more carbon atoms from the viewpoint of reducing the release of panobinostat or a salt thereof and therefore improving retentivity thereof in blood.

Lipids other than phospholipids may be lipids containing no phosphoric acid, and examples thereof include, but are not particularly limited to, glycerolipid which does not contain a phosphoric acid moiety in the molecule, and sphingolipid which does not contain a phosphoric acid moiety in the molecule. In the present invention, the term "lipids other than phospholipids" also encompasses derivatives of lipids other than phospholipids in which modifications have been made to lipids other than phospholipids.

Examples of cholesterols include cholesterol which contains cyclopentahydrophenanthrene as a basic skeleton whose carbon atoms are partially or completely hydrogenated and derivatives thereof. For example, cholesterol is mentioned. In a case where the average particle size of the lipid particle decreases to 100 nm or less, the curvature of the lipid membrane becomes higher. The deformation of the membrane arranged in the lipid particle also becomes larger. It is effective to add cholesterol or the like in order to fill the deformation of the membrane caused by lipid (membrane-stabilizing effect).

In connection with the lipid particle, the addition of cholesterol is expected to lower the fluidity of the membrane of the lipid particle, for example, by filling the gaps in the membrane of the lipid particle.

The content of cholesterols with respect to the total amount of lipids constituting the lipid particle according to the present invention is preferably 10 mol % to 50 mol %, more preferably 20 mol % to 45 mol %, still more preferably 30 mol % to 45 mol %, and particularly preferably 35 mol % to 45 mol %.

The lipid particles in the present invention may contain a lipid modified with a hydrophilic polymer.

Examples of the hydrophilic polymer include polyethylene glycols, polyglycerins, polypropylene glycols, polyvinyl alcohols, a styrene-maleic acid anhydride alternating copolymer, polyvinylpyrrolidone, and synthetic polyamino acid. The above-mentioned hydrophilic polymers may be used alone or in combination of two or more thereof.

Among these, from the viewpoint of retentivity in blood of a composition, preferred are polyethylene glycols, polyglycerins, or polypropylene glycols are preferable, and polyethylene glycol (PEG), polyglycerin (PG), or polypropylene glycol (PPG) is more preferable. Polyethylene glycol (PEG) is still more preferable from the viewpoint of versatility and retentivity in blood.

The weight-average molecular weight of polyethylene glycol is not particularly limited, but it is 500 to 10,000 daltons, preferably 1,000 to 7,000 daltons, and more preferably 2,000 to 5,000 daltons.

In the first aspect of the lipid particle in the present invention, it is preferable to use a PEG-modified lipid (polyethylene glycol lipid), together with the main lipid contained in the lipid particle. Examples of the polyethylene glycol lipid include 1,2-distearoyl-3-phosphatidylethanolamine polyethylene glycols such as 1,2-distearoyl-3-phosphatidylethanolamine-PEG2000 (manufactured by Nippon Oil & Fats Co., Ltd.), 1,2-distearoyl-3-phosphatidylethanolamine-PEG5000 (manufactured by Nippon Oil & Fats Co., Ltd.), and distearoyl glycerol-PEG2000 (manufactured by Nippon Oil & Fats Co., Ltd.).

The percentage of the polyethylene glycol lipid in the total lipids constituting the lipid particle is generally 0.01 to 10 mol %, preferably 0.05 to 8 mol %, and more preferably 0.1 to 7 mol %. The percentage of the polyethylene glycol lipid is also preferably 5 mol % or less and more preferably 1 mol % or less.

In the second aspect of the lipid particle in the present invention, it is preferred that the lipid particle is substantially free of the polyethylene glycol lipid.

It is also preferred that the lipid particle in the present invention contains an anionic lipid together with the main lipid contained in the lipid particle. Examples of the anionic lipid include a lipid having a phosphatidylglycerol, such as 1,2-dipalmitoyl-sn-glycero-3-phosphoglycerol, sodium salt (COATSOME MG-6060LS, manufactured by NOF Corporation); a lipid having a phosphatidic acid, such as 1,2- dimyristoyl-sn-glycero-3-phosphatidic acid, sodium salt (COATSOME MA-6060LS, manufactured by NOF Corporation); a lipid having a phosphatidylserine, such as 1,2-dipalmitoyl-sn-glycero-3-phospho-L-serine, sodium salt (COATSOME MS-6060LS, manufactured by NOF Corporation); a lysophospholipid such as 1-stearoyl-2-lyso-sn-glycero-3-phosphocholine (COTSOME MC-80H, manufactured by NOF Corporation); a steroid derivative having an anionic group, such as cholesteryl hemisuccinate (CHEMS, manufactured by Avanti Polar Lipids, Inc.); and a fatty acid such as stearic acid.

The percentage of the anionic lipid in the total lipids constituting the lipid particle is not particularly limited, but it is 0.01 to 50 mol %, preferably 0.05 to 30 mol %, and more preferably 0.1 to 10 mol %. The anionic lipid may be used alone or in combination with the PEG lipid. In addition, the hydrophilic polymers may be used alone or in combination of two or more thereof.

In addition to the foregoing components, a hydrophilic polymer or the like for improving retentivity in blood, fatty acid, diacetyl phosphate, or the like as a membrane structure stabilizer, or α-tocopherol or the like as an antioxidant may be added to the lipid particle. In the present invention, it is preferable not to use an additive such as a dispersion aid which is not recognized for use in intravenous injection in medical use, for example, a surfactant.

(Panobinostat)

The lipid particle composition according to the embodiment of the present invention contains panobinostat or a salt thereof as a drug.

Panobinostat is a hydroxamic acid derivative used for the treatment of multiple myeloma and is one of non-selective histone deacetylase inhibitors. The chemical structure of panobinostat is shown below.

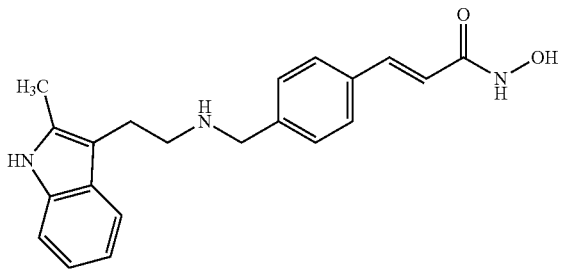 [SMILES: Cc1[nH]c2ccccc2c1CCNCc1ccc(/C=C/C(=O)NO)cc1]

The salt of panobinostat may be, for example, a salt in a basic group such as a commonly known amino group.

Examples of the salt in a basic group include salts with mineral acids such as hydrochloric acid, hydrobromic acid, phosphoric acid, boric acid, nitric acid, and sulfuric acid; salts with organic carboxylic acids such as formic acid, acetic acid, lactic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylenesulfonic acid, and naphthalenesulfonic acid. An example of the salt of panobinostat is a lactate salt of panobinostat, the structure of which is shown below.

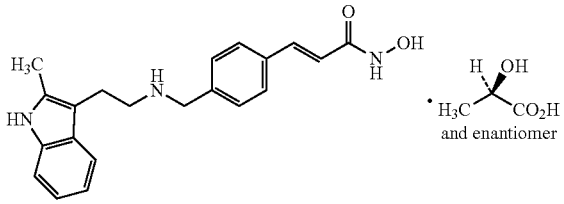

(Panobinostat or Salt Thereof Contained in Lipid Particle Composition)

In the lipid particle composition according to the embodiment of the present invention, the state of the presence of panobinostat or a salt thereof in the lipid particle is not particularly limited, but it is presumed that, from the difference in accumulation properties of panobinostat or a salt thereof in the bone marrow with an empty liposome, which will be described later, at least a part of panobinostat or a salt thereof is present in a form that affects recognition by proteins in blood or cells such as macrophages, which recognize lipid particles. That is, it is presumed that a part of the panobinostat or the salt thereof is present on the membrane surface of the lipid particle or in a state affecting the mobility of lipid molecules present on the membrane surface.

In the lipid particle composition according to the embodiment of the present invention, as to the presence state of panobinostat or a salt thereof in a case where the panobinostat or the salt thereof to be encapsulated is in a high concentration, as can be read from the TEM image in FIG. 1, a part of the panobinostat or the salt thereof may be present as a solidified material on at least a part of the surface and the inside of the lipid particle. Even in such a case, the rest of the panobinostat or the salt thereof may be present in a dissolved state in the inner water phase of the lipid particle. Here, with regard to the term "dissolved state", a drug is deemed to have been encapsulated in a dissolved state in a case where the amount of the drug filled with respect to the volume of the lipid particle is below the saturation solubility of the drug in the composition liquid of the inner water phase. In addition, even in a case where the amount of the drug filled is above the saturation solubility thereof, a case where drug crystals are not observed by Cryo-TEM [transmission electron microscope (TEM) observation of a frozen sample] or diffraction patterns due to crystal lattices are not observed by XRD measurement, it can be deemed that most of the drug encapsulated in the lipid particle is dissolved and present in a dissolved state.

In the present invention, the solidified material means a solid which can be observed by a transmission electron microscope (TEM).

(Panobinostat or Salt Thereof/Lipid Ratio)

The panobinostat or a salt thereof/lipid ratio in the lipid particle in the present invention is 10 to 500 mg/mmol, preferably 20 to 400 mg/mmol, and more preferably 30 to 300 mg/mmol. In a case of including a salt of panobinostat, the panobinostat or a salt thereof/lipid ratio is calculated in an amount converted as panobinostat. In addition, the lipid in the panobinostat or a salt thereof/lipid ratio means all the lipids which constitute a lipid particle, in which the lipid also includes cholesterol and lysophospholipid.

(Lipid Particle Composition)

In the lipid particle composition according to the embodiment of the present invention, the area ratio represented by Formula 1 up to the infinite time after single administration of the lipid particle composition of 4 mg/kg as the panobinostat amount to the tail vein of the mouse is preferably greater than 1, more preferably 2 or more, still more preferably 3 or more, even more preferably 5 or more, particularly preferably 10 or more, and most preferably 12 or more.

(area under bone marrow concentration-time curve)/
(area under gastrointestinal tract concentration-
time curve)    Formula 1:

In the lipid particle composition according to the embodiment of the present invention, the bone marrow accumulation rate (% ID/g) represented by Formula 2 is preferably 10% ID/g or more, more preferably 15% ID/g or more, still more preferably 20% ID/g or more, even more preferably 30% ID/g or more, and particularly preferably 40% ID/g or more. The bone marrow accumulation rate shown in the Examples of the present invention is determined as a percentage (% injected dose/g) of lipid particles accumulated in bone marrow among the lipid particles administered per gram of femoral bone marrow, 72 hours after administration of a lipid particle composition containing panobinostat (6 mg/kg or 4 mg/kg in terms of the amount of panobinostat), which is labeled with DiI (1,1'-dioctadecyl-3,3,3',3'-tetramethylindocarbocyanine perchlorate), to the tail vein of a mouse, and is represented by Formula 2.

Bone marrow accumulation rate (% ID/g)=DiI concentration in bone marrow (ng/g)/(DiI concentration in administration liquid (ng/mL)×dose (mL))×100    Formula 2:

In order to determine the bone marrow accumulation rate (% ID/g), a label different from DiI used in the present invention may be used. Alternatively, the bone marrow accumulation rate may be determined by tracing the lipids constituting the lipid particle without using a label. Further, the bone marrow accumulation rate may also be determined using a method of labeling the lipid particle composition later as shown in Example 25, in addition to the method of labeling the lipid particle composition in advance as shown in the Examples of the present invention.

The lipid particle composition according to the embodiment of the present invention can include lipid particles containing panobinostat or a salt thereof, and an aqueous solvent for dispersing the lipid particles.

In connection with the route of administration, the lipid particle composition according to the embodiment of the present invention may contain at least one of a tonicity agent, a stabilizer, an antioxidant, or a pH adjusting agent which is pharmaceutically acceptable.

The tonicity agent is not particularly limited and examples thereof include inorganic salts such as sodium chloride, potassium chloride, sodium hydrogen phosphate, sodium dihydrogen phosphate, and potassium dihydrogen phosphate; polyols such as glycerol, mannitol, and sorbitol; and sugars such as glucose, fructose, lactose, and sucrose.

The stabilizer is not particularly limited and examples thereof include sugars such as glycerol, mannitol, sorbitol, lactose, and sucrose.

The antioxidant is not particularly limited and examples thereof include ascorbic acid, uric acid, tocopherol homologues (for example, vitamin E, four tocopherol isomers α, β, γ, and δ), cysteine, and ethylenediaminetetraacetic acid (EDTA), propyl gallate, dibutylhydroxytoluene (BHT), butylhydroxyanisole (BHA), and sodium pyrosulfite. Stabilizers and antioxidants may be respectively used alone or in combination of two or more thereof.

Examples of the pH adjusting agent include sodium hydroxide, citric acid, acetic acid, triethanolamine, sodium hydrogen phosphate, sodium dihydrogen phosphate, and potassium dihydrogen phosphate.

The lipid particle composition according to the embodiment of the present invention may contain an organic solvent, collagen, polyvinyl alcohol, polyvinyl pyrrolidone, a carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, gelatin, agar, diglycerin, propylene glycol, polyethylene glycol, vaseline, paraffin, stearyl alcohol, stearic acid, human serum albumin (HSA), mannitol, sorbitol, lactose, phosphate buffered saline (PBS), sodium chloride, sugars, a biodegradable polymer, a serum-free medium, each of which is pharmaceutically acceptable, or an additive which is acceptable as a pharmaceutical additive.

The container in which the lipid particle composition according to the embodiment of the present invention is filled is not particularly limited, and it is preferably made of a material having a low oxygen permeability. Examples of the container include a plastic container, a glass container, and a bag made of a laminate film having an aluminum foil, an aluminum-deposited film, an aluminum oxide-deposited film, a silicon oxide-deposited film, a polyvinyl alcohol, an ethylene-vinyl alcohol copolymer, polyethylene terephthalate, polyethylene naphthalate, polyvinylidene chloride, or the like as a gas barrier layer. If necessary, light may be shielded by adopting a bag or the like using a colored glass, an aluminum foil, an aluminum-deposited film, or the like.

In the container in which the lipid particle composition is filled, in order to prevent oxidation due to oxygen present in the space in the container, it is preferable to replace gases in the container space and drug solution with inert gases such as nitrogen. For example, the lipid particle composition can be filled in such a manner that an injection solution is bubbled with nitrogen, and then the filling of the injection solution into a container is carried out under a nitrogen atmosphere.

It is also preferable to carry out freeze-drying in order to prevent the decomposition of the lipid and drug substance in the lipid particle composition. For example, it is possible to disperse lipid particles in a water phase containing sucrose and carry out freeze-drying.

(Method for Producing Lipid Particle Composition)

The method for producing the lipid particle composition according to the embodiment of the present invention is not particularly limited. For example, the lipid particle composition according to the embodiment of the present invention can be produced by the following steps:

(a) preparation of an oil phase;
(b) preparation of a water phase;
(c) lipid particle formation by emulsification;
(d) particle size regulation by an extruder;
(e) replacement of lipid particle outer water phase liquid by dialysis;
(f) encapsulation of panobinostat in lipid particles by remote loading; and
(g) removal of outer water phase panobinostat by dialysis.

<(a) Preparation of Oil Phase>

(a) In preparation of an oil phase, individual components (phospholipid, cholesterol, and the like) constituting the lipid particle and an organic solvent are mixed, and the mixture is heated to dissolve the above-mentioned components, whereby an oil phase can be produced.

Although the organic solvent used in the oil phase is not particularly limited, for example, a water-soluble organic solvent which is optionally mixed with water can be used.

Examples of the water-soluble organic solvent include alcohols such as methanol, ethanol, n-propanol, isopropanol, n-butanol, isobutanol, and t-butanol; glycols such as glycerin, ethylene glycol, and propylene glycol; and polyalkylene glycols such as polyethylene glycol. Among these, alcohols are preferred. The alcohol is preferably at least one selected from ethanol, methanol, 2-propanol, or t-butanol, more preferably at least one selected from ethanol, 2-propanol, or t-butanol, and still more preferably ethanol.

The concentration of the lipid is not particularly limited and can be appropriately adjusted.

<(b) Preparation of Water Phase>

Water (distilled water, water for injection, or the like), physiological saline, an aqueous solution of various buffer solutions or sugars, or a mixture thereof (aqueous solvent) can be used as the water phase. In the present invention, it is preferable to use an aqueous solution containing an ammonium salt as the water phase, in a case where panobinostat is encapsulated in lipid particles by remote loading which will be described later.

The buffer solution is not limited to organic and inorganic buffer solutions, and a buffer solution having a buffering action in the vicinity of a pH close to that of the body fluid is suitably used and examples thereof include a phosphate buffer solution, a Tris buffer solution, a citrate buffer solution, an acetate buffer solution, and a Good's buffer solution. The inner water phase of the lipid particle may be an aqueous solution in which the lipid particles are dispersed in a case of producing lipid particles, or may be water, physiological saline, an aqueous solution of various buffer solutions or sugars, or a mixture thereof which is newly added. The water used as an outer water phase or an inner water phase is preferably free from impurities (dust, chemicals, or the like).

The physiological saline refers to an inorganic salt solution adjusted to be isotonic with the human body fluid, and may further have a buffering function. Examples of the physiological saline include saline containing 0.9 w/v % (mass/volume percent) of sodium chloride, PBS, and Tris buffered physiological saline.

In the present invention, the water phase includes both an outer water phase and an inner water phase.

The outer water phase in the present invention means an aqueous solution in which lipid particles are dispersed. For example, in a case of an injection, a solution occupying the outside of the lipid particle of a dispersion liquid of lipid particles packaged and stored in a vial or prefilled syringe becomes an outer water phase. Also, similarly for a liquid to be dispersed at the time of use in a case of being administered by means of an attached dispersion solution or other solutions, a solution occupying the outside of the lipid particle of a dispersion liquid of lipid particles becomes an outer water phase.

The inner water phase in the present invention refers to a water phase in closed vesicles separated by lipid bilayer membranes of lipid particles.

<(c) Lipid Particle Formation by Emulsification>

In the emulsifying step, an oil phase where at least one lipid has been dissolved in an organic solvent and a water phase are mixed to prepare an aqueous solution containing lipids, which can be then emulsified with stirring. An oil phase where lipid has been dissolved in an organic solvent and a water phase are mixed, stirred, and emulsified to thereby prepare an emulsion where the oil phase and the water phase are emulsified in an O/W type (oil-in-water type). After mixing, lipid particles are formed by removing a portion or all of the organic solvent derived from the oil phase by evaporation. Alternatively, a portion or all of the organic solvent in the oil phase is evaporated in the course of the stirring-emulsification to form lipid particles.

As a method of stirring, ultrasonic waves or mechanical shearing force is used for particle miniaturization. In addition, extruder processing or microfluidizer processing of allowing to pass through a filter having a certain pore size can be carried out for uniformity of particle sizes. Use of an extruder or the like can result in decomposition of secondarily formed multivesicular lipid particles into univesicular lipid particles.

The emulsifying step is not limited as long as it is a step of emulsification, but it is preferably a step of applying a high shearing force and performing microparticulation with an emulsifying step including an organic solvent. If necessary, evaporation (desolvation) of the organic solvent used in the emulsifying step may be carried out to form lipid particles.

The liquid temperature in the emulsifying step in a case of producing lipid particles can be appropriately adjusted, but the liquid temperature at the time of mixing an oil phase and a water phase is preferably higher than or equal to a phase transition temperature of the lipid to be used. For example, in a case where a lipid having a phase transition temperature of 35° C. to 40° C. is used, the liquid temperature is preferably set to 35° C. to 70° C.

In the emulsifying step, the organic solvent and water may be evaporated from the aqueous solution containing lipid particles. As to the evaporation referred to herein, a portion or all of the organic solvent derived from the oil phase and the water derived from the water phase may be forcibly removed as an evaporation step, or a portion or all of the organic solvent derived from the oil phase and the water derived from the water phase may evaporate naturally during the course of stirring-emulsification.

The method of evaporation is not particularly limited. For example, at least one of a step of heating to evaporate an organic solvent and water, a step of continuing the standing or slow stirring after emulsification, or a step of carrying out vacuum degassing may be carried out.

<(d) Particle Size Regulation by Extruder>

The obtained lipid particles can be made uniform in particle size by using dialysis, filtration, extrusion processing, or the like.

The extrusion processing means a step of passing lipid particles through a filter having a fine pore to apply a physical shear force, thereby carrying out microparticulation of the lipid particles. In a case where the lipid particles are passed through, rapid microparticulation thereof may be achieved by incubating the lipid particle dispersion liquid and the filter at a temperature higher than or equal to the phase transition temperature of the membrane constituting the lipid particle.

In addition, the particle size regulation by an extruder may or may not be carried out.

<(e) Replacement of Lipid Particle Outer Water Phase Liquid by Dialysis>

In the present invention, in a case where panobinostat is encapsulated in the lipid particles by remote loading, the lipid particle outer water phase liquid may be replaced by dialysis. An aqueous solution of 0.1% to 5 mass % NaCl can be used as a dialysis liquid which is not particularly limited. Dialysis of the lipid particle liquid using the above-mentioned dialysis liquid can provide lipid particles in which the ammonium salt present in the outer water phase is removed and the outer water phase is replaced with the dialysis liquid.

<(f) Encapsulation of Panobinostat in Lipid Particles by Remote Loading Method>

In the present invention, it is preferable to encapsulate panobinostat in lipid particles by a remote loading method.

In the present invention, the remote loading method refers to a method of producing an empty liposome in which a drug is not encapsulated and then adding the drug to the liposome outer liquid to introduce the drug into the liposome. The method of remote loading is not particularly limited and an example thereof is a method using a citrate buffer solution or ammonium sulfate.

In the remote loading method, the drug added to the outer liquid is actively transferred to lipid particles and incorporated into the lipid particles. A solubility gradient, an ion gradient, a pH gradient, or the like is used as the driving force. For example, there is a method of introducing a drug into lipid particles using an ion gradient formed across a lipid particle membrane. For example, there is a technique of adding a drug into lipid particles that are preformed by the remote loading method using a $Na^+/K^+$ concentration gradient.

Among the ion gradients, a proton concentration gradient is generally used. For example, there is an aspect in which the inner (inner water phase) pH of the lipid particle membrane has a pH gradient lower than the outer (outer water phase) pH, using citric acid. Specifically, the pH gradient can be formed by, for example, an ammonium ion gradient and/or a concentration gradient of an organic compound having an amino group that can be protonated.

The ammonium ion source is not particularly limited, but a water-soluble ammonium salt is suitably used and examples thereof include ammonium sulfate, ammonium chloride, ammonium formate, ammonium succinate, and ammonium acetate.

<(g) Removal of Outer Water Phase Panobinostat by Dialysis>

The panobinostat-encapsulated lipid particle liquid may be subjected to dialysis to remove panobinostat not contained in the lipid particles. For example, by subjecting the panobinostat-encapsulated lipid particle liquid to dialysis, using a predetermined concentration of sucrose/histidine buffer as a dialysis liquid, the panobinostat present in the outer water phase can be removed to obtain a lipid particle composition in which the outer water phase is replaced with the dialysis liquid.

<Sterile Filtration>

The lipid particle composition obtained above is preferably subjected to sterile filtration. Regarding the filtration method, it is possible to remove unwanted materials from an aqueous solution containing lipid particles by using a hollow fiber membrane, a reverse osmosis membrane, a membrane filter, or the like. In the present invention, it is preferable to filter the lipid particle composition through a filter having a sterilizable pore size (preferably a 0.2 μm filtration sterilization filter).

To prevent an effect of deformation of lipid particles on the average particle size, the sterile filtration step and the below-described aseptic filling step are preferably carried out at a temperature lower than or equal to the phase transition temperature of the lipid constituting the lipid particle. For example, in a case where the phase transition temperature of the lipid is around 50° C., the sterile filtration step and the below-described aseptic filling step are carried out at temperature of preferably about 0° C. to 40° C., and more specifically about 5° C. to 30° C.

<Aseptic Filling>

The lipid particle composition obtained after sterile filtration is preferably aseptically filled for medical applications. Known methods can be applied for aseptic filling. A lipid particle composition suitable for medical applications can be prepared by aseptically filling the lipid particle composition in a container.

(Pharmaceutical Composition)

The lipid particle composition according to the embodiment of the present invention can be used as a pharmaceutical composition. That is, according to the present invention, there is provided a pharmaceutical composition including the lipid particle composition according to the embodiment of the present invention.

The administration method of the pharmaceutical composition according to the embodiment of the present invention is preferably parenteral administration. Examples of the parenteral administration include intravenous injection such as intravenous drip, intramuscular injection, intraperitoneal injection, subcutaneous injection, intraocular injection, and intrathecal injection. The administration method of the pharmaceutical composition may be, for example, administration by syringe or intravenous drip.

The dose and frequency of administration of panobinostat or a salt thereof as a drug contained in the lipid particle composition can be generally set in the range of 0.01 mg/kg/day to 100 mg/kg/day in terms of the mass of panobinostat or a salt thereof, but the lipid particle composition according to the embodiment of the present invention is not limited to these dosages.

The pharmaceutical composition according to the embodiment of the present invention can be preferably used as an anticancer agent.

The type of cancer to which the pharmaceutical composition according to the embodiment of the present invention is applied is not particularly limited, and examples thereof include multiple myeloma, acute myeloid leukemia, chronic mycloid leukemia, acute lymphocytic leukemia, adult T cell leukemia, bone marrow metastatic cancer, osteosarcoma, chronic myelomonocytic leukemia, Hodgkin's lymphoma, cutaneous T cell lymphoma, breast cancer, prostate cancer, uterine body cancer, ovarian cancer, lung cancer, gastric cancer (gastric adenocarcinoma), non-small cell lung cancer, pancreatic cancer, cervical squamous cell carcinoma, esophagus cancer, bladder cancer, melanoma, colon cancer, renal cell cancer, non-Hodgkin's lymphoma, and urothelial cancer.

EXAMPLES

Hereinafter, the present invention will be described in detail by way of Examples. However, the present invention is not limited to the Examples.

Preparation of Lipid Particle Composition

Example 1

(a) Preparation of Oil Phase 0.495 g of 1,2-diarachidonoyl-sn-glycero-3-phosphocholine (manufactured by Nippon Fine Chemical Co., Ltd., hereinafter referred to as C20PC), 0.153 g of PEG phospholipid (SUNBRIGHT DSPE-020CN, manufactured by NOF Corporation, hereinafter referred to as DSPE-PEG), and 0.153 g of cholesterol were weighed. In order to label lipid particles with DiI (1,1'-dioctadecyl-3,3,3',3'-tetramethylindocarbocyanine perchlorate), an amount of DiI, which was 0.2 mol % with respect to total lipids, was weighed and dissolved in ethanol. Ethanol was added to the DiI ethanol solution to make a total volume of 11.25 mL, and 3.75 mL of ethyl acetate was further added thereto. The weighed lipid and this organic solvent were mixed and heated to 60° C. to dissolve the lipid, thus preparing an oil phase.

(b) Preparation of Water Phase

A water phase was prepared by dissolving 0.9 g of ammonium sulfate in 40 g of water.

(c) Lipid Particle Formation by Emulsification

The water phase prepared in (b) was heated to 70° C., the whole of the oil phase prepared in (a) was added thereto (volume ratio: water phase/oil phase=8/3), and then two phases were mixed using an emulsification machine (Excel Auto homogenizer ED-3, manufactured by Nippon Seiki Seisakusho Co., Ltd.) at 3000 rpm (rotation per minute: 1/60 $s^{-1}$) for 30 minutes. Subsequently, the organic solvent and water were evaporated by continuing the stirring at 300 rpm while heating at 65° C., and in a case where the liquid was concentrated to 15 g, the heating and stirring were stopped and the evaporation was stopped.

(d) Particle Size Regulation by Extruder

Although the particle size regulation was not carried out in Example 1, Examples having a description of the filter size in the column of "Particle size regulation" among the Examples described in the table which will be given later were subjected to the particle size regulation in the following manner. The liquid obtained in (c) was subjected to the particle size regulation by sequentially passing it through a filter using an extruder (Mini Extruder, manufactured by Avanti Polar Lipids, Inc.) under heating at 70° C. As to the size of the filter, a filter having the filter size described in the column of "Particle size regulation" of each table was used. In Example described for multiple filter sizes, the particle size regulation was carried out with a large pore size filter, and then the particle size regulation was carried out with a small pore size filter.

(e) Replacement of Lipid Particle Outer Water Phase Liquid by Dialysis

An aqueous solution of 2.43 mass % NaCl was used as a dialysis liquid. Using this dialysis liquid, the liquid obtained in (c) or (d) was subjected to dialysis at room temperature to remove ammonium sulfate present in the outer water phase to obtain lipid particles in which the outer water phase was replaced with the dialysis liquid.

(f) Encapsulation of Panobinostat in Lipid Particles by Remote Loading

Water for injection was added to panobinostat (manufactured by APAC Pharmaceutical, LLC.) to 10 mg/mL. Further, while stirring the liquid well, an 8 mol/L HCl solution was added to adjust the pH to about 3 to dissolve panobinostat. Lipid particles were added to the resulting panobinostat solution at a volume ratio of 1/1, followed by heating at 60° C. for 120 minutes.

(g) Removal of Outer Water Phase Panobinostat by Dialysis

A sucrose/histidine buffer consisting of 9.4 mass % sucrose and 10 mmol/L histidine was prepared as a dialysis liquid. Using this dialysis liquid, the liquid obtained in (f) was subjected to dialysis at room temperature to remove panobinostat present in the outer water phase to obtain panobinostat-containing lipid particles in which the outer water phase was replaced with the dialysis liquid.

Example 2

Panobinostat-contaiinng lipid particles were obtained in the same manner as in Example 1, except that the amount of DSPE-PEG used was 0.0153 g.

Examples 3 to 13

Panobinostat-containing lipid particles were obtained in the same manner as in Example 1, except that the lipid composition described in the table given later was used. In the table given later, SM indicates sphingomyelin (COATSOME NM-10, manufactured by NOF Corporation), and DHSM indicates dihydrosphingomyelin (a hydrogenated synthetic product of COATSOME NM-10 (manufactured by NOF Corporation)).

Example 14

(a) Preparation of Oil Phase 0.420 g of sphingomyelin (COATSOME NM-10, manufactured by NOF Corporation, hereinafter referred to as SM), 0.014 g of PEG phospholipid (SUNBRIGHT DSPE-020CN, manufactured by NOF Corporation, hereinafter referred to as DSPE-PEG), and 0.155 g of cholesterol were weighed. In order to label lipid particles with DiI (1,1'-dioctadecyl-3,3,3',3'-tetramethylindocarbocyanine perchlorate), an amount of DiI, which was 0.2 mol % with respect to total lipids, was weighed and dissolved in ethanol. Ethanol was added to the DiI ethanol solution to make a total volume of 11.25 mL, and 3.75 mL of ethyl acetate was further added thereto. The weighed lipid and this organic solvent were mixed and heated to 70° C. to dissolve the lipid, thus preparing an oil phase.

(b) Preparation of Water Phase

A water phase was prepared by dissolving 0.9 g of ammonium sulfate in 40 g of water.

(c) Lipid Particle Formation by Emulsification

The water phase prepared in (b) was heated to 70° C., followed by stirring with a magnetic stirrer, and the whole of the oil phase prepared in (a) was added thereto, followed by stirring for 30 seconds (volume ratio: water phase/oil phase=8/3). Subsequently, the organic solvent and water were evaporated by continuing the stirring at 300 rpm while heating at 65° C., and in a case where the liquid was concentrated to 15 g, the heating and stirring were stopped and the evaporation was stopped.

(d) Particle Size Regulation by Extruder

The liquid obtained in (c) was subjected to the particle size regulation by sequentially passing it through a filter using an extruder (Mini Extruder, manufactured by Avanti Polar Lipids, Inc.) under heating at 70° C. As to the size of the filter, a filter having the filter size described in the column of "Particle size regulation" of each table was used.

In Example described for multiple filter sizes, the particle size regulation was carried out with a large pore size filter, and then the particle size regulation was carried out with a small pore size filter.

(e) Replacement of Lipid Particle Outer Water Phase Liquid by Dialysis

A 720 mM NaCl aqueous solution was used as a dialysis liquid. Using this dialysis liquid, the liquid obtained in (d) was subjected to dialysis at room temperature to remove ammonium sulfate present in the outer water phase to obtain lipid particles in which the outer water phase was replaced with the dialysis liquid.

(f) Encapsulation of Panobinostat in Lipid Particles by Remote Loading

Water for injection was added to panobinostat (manufactured by APAC Pharmaceutical, LLC.) to 4 mg/mL. Further, while stirring the liquid well, an 8 mol/L HCl solution was added to adjust the pH to about 4 to dissolve panobinostat. The panobinostat solution, 720 mM NaCl aqueous solution, and lipid particles were mixed at a volume ratio of 5/3/2 and then heated at 60° C. for 120 minutes.

(g) Removal of Outer Water Phase Panobinostat by Dialysis

A sucrose/histidine buffer consisting of 9.4 mass % sucrose and 10 mmol/L histidine was prepared as a dialysis liquid. Using this dialysis liquid, the liquid obtained in (f) was subjected to dialysis at room temperature to remove panobinostat present in the outer water phase to obtain panobinostat-containing lipid particles in which the outer water phase was replaced with the dialysis liquid.

Examples 15 to 25

Panobinostat-containing lipid particles were obtained in the same manner as in Example 14 using the lipid compositions described in Tables 2 to 4. In Example 25, lipid particles were prepared without addition of DiI. In Tables 2 to 4, C20PC indicates 1,2-diarachidonoyl-sn-glycero-3-phosphocholine (manufactured by Nippon Fine Chemical Co., Ltd.); HSPC indicates hydrogenated soybean phosphatidylcholine (COATSOME NC-21, manufactured by NOF Corporation); DPPG indicates 1,2-dipalmitoyl-sn-glycero-3-phosphoglycerol, sodium salt (COATSOME MG-6060LS, manufactured by NOF Corporation); DPPA indicates 1,2-dimyristoyl-sn-glycero-3-phosphatidic acid, sodium salt (COATSOME MA-6060LS, manufactured by NOF Corporation); and DPPS indicates 1,2-dipalmitoyl-sn-glycero-3-phospho-L-serine, sodium salt (COATSOME MS-6060LS, manufactured by NOF Corporation). In step (f) of encapsulating panobinostat in lipid particles by remote loading, the panobinostat solution was 3.6 mg/mL in Examples 17 to 25. The mixing ratio of the panobinostat solution, the 720 mM NaCl aqueous solution, and the lipid particles was 8/5/5 in Example 16 and 2/1/1 in Examples 17 to 25.

Only in Example 22, the average particle size is 331 nm, which is larger than in other Examples. This is because the peak of the aggregate was observed in the vicinity of 1 μm in the particle size measurement by DLS, and the average particle size was calculated to be large. In Example 22, the absolute value of the zeta potential is small, and the electrostatic phase repulsion between particles is small. In addition, no material such as DSPE-PEG has been added that interferes with particle coalescence by steric repulsion. Although the bone marrow accumulation rate is high in Example 22, it can be said that other Examples are preferred aspects from the viewpoint of particle stability.

Example 25

In Example 25, DiI was not added at the time of (a) preparation of an oil phase, and staining with DiI was carried out on the lipid particles subjected to dialysis with a sucrose/histidine buffer in (g). 5 μL of 3 mg/mL DiI/ethanol solution was mixed with 500 μL of lipid particle liquid and the mixture was thoroughly stirred. Thereafter, using a gel filtration method (PD MiniTrap G-25, manufactured by GE Healthcare), the outer water phase was replaced with a sucrose/histidine buffer consisting of 9.4 mass % sucrose and 10 mmol/L histidine to remove excess DiI.

Comparative Example 1

Panobinostat was dissolved in a mixture of polyoxyl 35 castor oil (Kolliphore EL, manufactured by Sigma-Aldrich Co. LLC.) and polyethylene glycol 400 (manufactured by Wako Pure Chemical Industries, Ltd.) at a volume ratio of 1:4 while being irradiated with ultrasonic waves. The obtained solution and physiological saline were mixed at a volume ratio of 1:7 to obtain a 0.5 mg/mL panobinostat solution.

Comparative Example 2

Lipid particles were prepared by the same steps as (a) to (e) in Example 1 and further, in the same manner as (g) in Example 1, the outer water phase was replaced with the same solution as in Example 1, so that lipid particles containing no panobinostat were obtained.

Comparative Example 3

16.63 g of HSPC, 2.04 g of cholesterol, and 4.15 g of DSPE-PEG were weighed and dissolved, together with the amount of DiI that was 0.2 mol % with respect to total lipids, in 303.75 mL of ethanol and 101.25 mL of ethyl acetate to prepare an oil phase. 5.6 g of 100 mmol/L sodium dihydrogen phosphate, 37.6 g of 100 mmol/L disodium hydrogen phosphate, and 1037 g of water for injection were mixed to prepare a water phase. The oil phase was mixed with the water phase, and a DiI-labeled empty liposome was prepared using an emulsification method. The outer water phase was replaced with TFF using an aqueous solution of 0.09 mass % sodium chloride, and subsequently pemetrexed was encapsulated by a passive loading method. This was followed by dialysis with a sucrose/histidine buffer consisting of 9.4 mass % sucrose and 0.155 mass % histidine to obtain lipid particles containing pemetrexed.

Comparative Example 4

12.42 g of HSPC, 4.14 g of cholesterol, and 4.14 g of DSPE-PEG were weighed and dissolved, together with the amount of DiI that was 0.2 mol % with respect to total lipids, in 303.4 mL of ethanol and 101.25 mL of ethyl acetate to prepare an oil phase. 26.73 g of ammonium sulfate was dissolved in 1080 g of MilliQ water to prepare a water phase. A DiI-labeled empty liposome containing ammonium sulfate was prepared using an emulsification method. The outer water phase was replaced with TFF using a 417 mM sodium chloride aqueous solution, and subsequently doxorubicin hydrochloride was encapsulated by a remote loading method. This was followed by dialysis with a sucrose/histidine buffer consisting of 9.4 mass % sucrose and 0.155 mass % histidine to obtain lipid particles containing doxorubicin hydrochloride. The composition of lipid particles was referred to the composition described in the package insert of DOXIL injection 20 mg (2 mg/mL doxorubicin hydrochloride, 9.58 mg/mL HSPC, 3.19 mg/mL DSPE-PEG, and 3.19 mg/mL cholesterol). As a result of quantification, it was found to have 2.24 mg/mL doxorubicin hydrochloride, 11.5 mg/mL HSPC, 4.1 mg/mL DSPE-PEG, and 4.2 mg/mL cholesterol.

[Measurement and Evaluation of Physical Properties]

<Average Particle Size>

In the present invention, the particle size refers to a cumulant average particle size measured by a dynamic light scattering method. The average particle sizes of Examples and Comparative Examples described in each table are cumulant average particle sizes measured by a dynamic light scattering method using a concentrated system particle size analyzer FPAR-1000AS (manufactured by Otsuka Electronics Co., Ltd.) with an autosampler. The measurement results are shown in each table.

<Zeta Potential>

In the present invention, the zeta potential refers to a value measured by a laser Doppler method. The zeta potential of Examples described in each table is a value obtained by diluting a lipid particle liquid 20 times with a sucrose/histidine buffer consisting of 9.4 mass % sucrose and 10 mmol/L histidine, which is the same as the outer water phase, and measuring the zeta potential with a zeta potential/particle size measurement system ELSZ-2 (manufactured by Otsuka Electronics Co., Ltd.). The measurement results are shown in each table.

<API Concentration>

In the present invention, the API concentration described in each table is a value obtained by measuring the amount of panobinostat (free form) contained in lipid particles by high performance liquid chromatography (HPLC). Ultraviolet light (UV) at 279 nm was used for the detection of panobinostat.

<Lipid Concentration>

In the present invention, the lipid concentration described in each table is a total of the concentration of each lipid obtained by quantifying each lipid contained in lipid particles by HPLC (high performance liquid chromatography). A corona charged particle detector (Corona charged aerosol detector (CAD)) was used for the detection of lipids.

<Observation by Transmission Electron Microscope (TEM)>

The lipid particle composition of Example 1 was rapidly frozen and observed under cryo conditions using a universal TEM to obtain a TEM image. The obtained TEM image is shown in FIG. 1. From the TEM image of FIG. 1, it can be seen that solidified material of panobinostat is present on at least a part of the surface and the inside of the lipid particle.

<Measurement of Accumulation Rate of Lipid Particles in Bone Marrow>

ICR mice (male, 7 weeks old, ICR is an initial of Institute of Cancer Research) were used for the test. The panobinostat-containing lipid particles (6 mg/kg in terms of a drug amount) prepared in Examples 1 and 3 to 7 and labeled with a fluorescent dye (DiI) were administered from the tail vein of the animal. In addition, the panobinostat-containing lipid particles (4 mg/kg in terms of a drug amount) prepared in Examples 2 and 8 to 13 and labeled with a fluorescent dye (DiI) were administered from the tail vein of the animal. In addition, lipid particles not containing panobinostat (the same amount as in Example 1 in terms of a lipid amount), prepared in Comparative Example 2 and labeled with a fluorescent dye (DiI), were administered from the tail vein of the animal. In addition, lipid particles containing pemetrexed (1.5 mg/kg in terms of a drug amount), prepared in Comparative Example 3 and labeled with a fluorescent dye (DiI), were administered from the tail vein of the animal. In addition, lipid particles containing doxorubicin hydrochloride (16.7 mg/kg in terms of a drug amount), prepared in Comparative Example 4 and labeled with a fluorescent dye (DiI), were administered from the tail vein of the animal.

72 hours after administration of lipid particles, mice were dissected and femoral bone marrow was collected. With respect to the collected bone marrow, the concentration of DiI in the administration liquid and tissue was quantified using an HPLC (high performance liquid chromatography) fluorescence detector, and the bone marrow accumulation rate was calculated by Formula 2. Incidentally, the bone marrow accumulation rate is shown as a percentage of lipid particles accumulated in the bone marrow (% injected dose/g, also expressed as % ID/g), among the administered lipid particles per gram of bone marrow. The measurement results are shown in each table.

Bone marrow accumulation rate (% ID/g)=DiI concentration in bone marrow (ng/g)/(DiI concentration in administration liquid (ng/mL)×dose (mL))×100            Formula 2:

TABLE 1

| | Amount of lipid used [mol %] | | | | | Particle size regulation μm | Average particle size nm | Zeta potential mV | API concentration ppm | Lipid concentration mM | Lipid particle bone marrow accumulation rate % ID/g |
|---|---|---|---|---|---|---|---|---|---|---|---|
| | C20PC | HSPC | SM | DHSM | Cholesterol | DSPE-PEG | | | | | | |
| Example 1 | 56.5 | — | — | — | 38.3 | 5.2 | — | 218 | ND | 2880 | 26.8 | 31.6 |
| Example 2 | 59.4 | — | — | — | 40.1 | 0.5 | — | 169 | ND | 2427 | ND | 69.8 |
| Comparative Example 2 | 56.5 | — | — | — | 38.3 | 5.2 | — | 188 | ND | — | 49.0 | 6.7 |
| Comparative Example 3 | — | 76.0 | — | — | 18.9 | 5.1 | — | 68 | ND | 200 | 2.9 | 2.8 |
| Comparative Example 4 | — | 56.6 | — | — | 38.2 | 5.2 | — | 94 | ND | 2245 | 26.8 | 12.4 |
| Example 3 | 56.5 | — | — | — | 38.3 | 5.2 | — | 208 | −32.7 | 3280 | 20.9 | 36.2 |
| Example 4 | 59.0 | — | — | — | 39.9 | 1.1 | — | 209 | −24.9 | 3489 | 18.2 | 50.7 |

TABLE 1-continued

| | Amount of lipid used [mol %] | | | | | Particle size regulation μm | Average particle size nm | Zeta potential mV | API concentration ppm | Lipid concentration mM | Lipid particle bone marrow accumulation rate % ID/g |
|---|---|---|---|---|---|---|---|---|---|---|---|
| | C20PC | HSPC | SM | DHSM | Cholesterol | DSPE-PEG | | | | | |
| Example 5 | 59.4 | — | — | — | 40.1 | 0.5 | — | 194 | −31.3 | 3924 | 18.3 | 70.8 |
| Example 6 | — | — | 59.4 | — | 40.1 | 0.5 | — | 196 | −21.4 | 3874 | 26.3 | 51.4 |
| Example 7 | — | — | — | 59.3 | 40.2 | 0.5 | — | 230 | −23.1 | 2513 | 24.9 | 41.4 |
| Example 8 | 59.4 | — | — | — | 40.1 | 0.5 | — | 177 | −28.1 | 2288 | 18.6 | 60.8 |
| Example 9 | 59.4 | — | — | — | 40.1 | 0.5 | 0.2 | 166 | −24.3 | 3819 | 26.9 | 57.4 |
| Example 10 | — | — | 59.4 | — | 40.1 | 0.5 | — | 185 | −30.1 | 1900 | 20.6 | 60.6 |
| Example 11 | — | — | 59.4 | — | 40.1 | 0.5 | 0.2 | 182 | −17.3 | 1417 | 23.6 | 33.3 |
| Example 12 | — | — | 59.4 | — | 40.1 | 0.5 | 0.2/0.1 | 141 | −19.3 | 1572 | 21.3 | 23.0 |
| Example 13 | — | — | 59.4 | — | 40.1 | 0.5 | 0.2/0.05 | 102 | −18.4 | 2257 | 21.5 | 18.8 |

TABLE 2

| | Amount of lipid used [mol %] | | | | | | Particle size regulation μm | Average particle size nm | Zeta potential mV | API concentration ppm | Lipid concentration mH | Lipid particle bone marrow accumulation rate % ID/g |
|---|---|---|---|---|---|---|---|---|---|---|---|---|
| | SM | Cholesterol | DSPE-PEG | DPPG | DPPA | DPPS | | | | | | |
| Example 14 | 59.5 | 40.0 | 0.5 | — | — | — | 0.2 | 163 | −18.3 | 2055 | 17.0 | 39.2 |
| Example 15 | 55.5 | 40.0 | 0.5 | 4.0 | — | — | 0.2 | 168 | −33.6 | 2126 | 17.6 | 48.4 |
| Example 16 | 55.5 | 40.0 | 0.5 | — | 4.0 | — | 0.2 | 159 | −32.4 | 2048 | 17.2 | 45.3 |
| Example 17 | 55.5 | 40.0 | 0.5 | — | — | 4.0 | 0.2 | 177 | −28.3 | 1991 | 15.6 | 41.7 |

TABLE 3

| | Amount of lipid used [mol %] | | | | | Particle size regulation μm | Average particle size nm | Zeta potential mV | API concentration ppm | Lipid concentration mM | Lipid particle bone marrow accumulation rate % ID/g |
|---|---|---|---|---|---|---|---|---|---|---|---|
| | SM | C20PC | HSPC | Cholesterol | DPPG | | | | | | |
| Example 18 | 58.0 | — | — | 40.0 | 2.0 | 0.2 | 174 | −28.7 | 2164 | 16.2 | 87.5 |
| Example 19 | 56.0 | — | — | 40.0 | 4.0 | 0.2 | 167 | −31.7 | 1882 | 16.6 | 112.6 |
| Example 20 | 54.0 | — | — | 40.0 | 6.0 | 0.2 | 181 | −27.0 | 1868 | 16.7 | 68.8 |
| Example 21 | 52.0 | — | — | 40.0 | 8.0 | 0.2 | 178 | −24.0 | 1959 | 16.6 | 74.7 |
| Example 22 | 60.0 | — | — | 40.0 | — | 0.2 | 331 | −4.4 | 2224 | 17.8 | 83.5 |
| Example 23 | — | 60.0 | — | 40.0 | — | 0.2 | 166 | −24.3 | 2308 | 15.5 | 93.8 |
| Example 24 | — | — | 60.0 | 40.0 | — | 0.2 | 182 | −25.0 | 2321 | 14.3 | 87.2 |

TABLE 4

| | Amount of lipid used [mol %] | | | Particle size regulation μm | Average particle size nm | Zeta potential mV | API concentration ppm | Lipid concentration mM | Lipid particle bone marrow accumulation rate % ID/g |
|---|---|---|---|---|---|---|---|---|---|
| | SM | Cholesterol | DSPE-PEG | | | | | | |
| Example 25 | 59.5 | 40.0 | 0.5 | 0.2 | 182 | −20.7 | 1946 | 13.8 | 64.5 |

The lipid particle compositions of Examples 1 to 25 of the present invention exhibited high bone marrow accumulation properties as compared with the lipid particle compositions of Comparative Examples 2 to 4.

From Examples 3 to 5 and 22 to 24, the smaller the amount of DSPE-PEG added, the better the accumulation properties in the bone marrow. In addition, from Examples 10 to 13, the larger the particle size, the better the ability to accumulate in the bone marrow, but on the other hand, even for small lipid particles of about 100 nm, higher bone marrow accumulation properties were obtained as compared with lipid particles that do not encapsulate panobinostat (empty liposomes). From Examples 14 to 17, the bone marrow accumulation properties were improved by the addition of anionic lipids.

The lipid particles encapsulating panobinostat are presumed to be highly accumulated in the bone marrow by being recognized by macrophages as shown in the subsequent analysis. All of the above-mentioned factors are thought to contribute indirectly to enhancing the bone marrow accumulation ability by affecting the ease of recognition from macrophages. For example, in a case where the zeta potential is lowered by the addition of an anionic lipid, there is an effect such as being easily recognized by a scavenger receptor of macrophages, which is considered to be linked to the improvement of bone marrow accumulation properties.

<Measurement of Tissue Concentration of Panobinostat>

The panobinostat-containing lipid particles (4 mg/kg in terms of a drug amount) prepared in Examples 1, 2, 14, and 19 were administered to ICR mice (male, 7 weeks old) from the tail vein. In addition, the panobinostat solution (5 mg/kg) prepared in Comparative Example 1 was intraperitoneally administered to ICR mice (male, 7 weeks old). Assuming the dose in the drug efficacy test, the dose of the panobinostat-containing lipid particles prepared in Examples 1, 2, 14, and 19 was set to the maximum tolerance dose in single administration, and the dose of the panobinostat solution prepared in Comparative Example 1 was set to the maximum tolerance dose for daily administration for 8 days.

Figure 2:
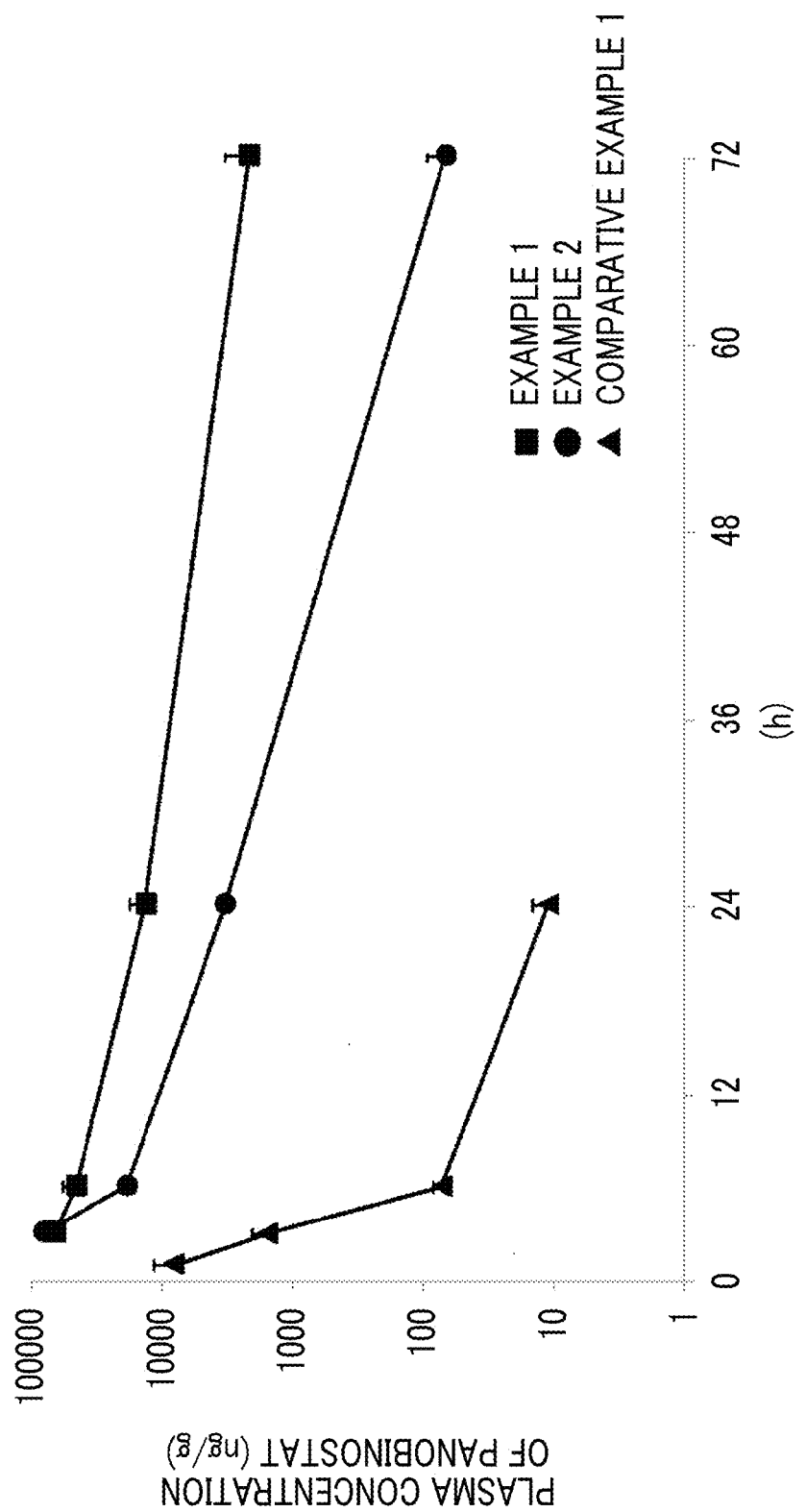
FIG. 2 shows the measurement results of a plasma concentration of panobinostat after the administration of the panobinostat-containing lipid particle or a panobinostat solution.
Figure 3:
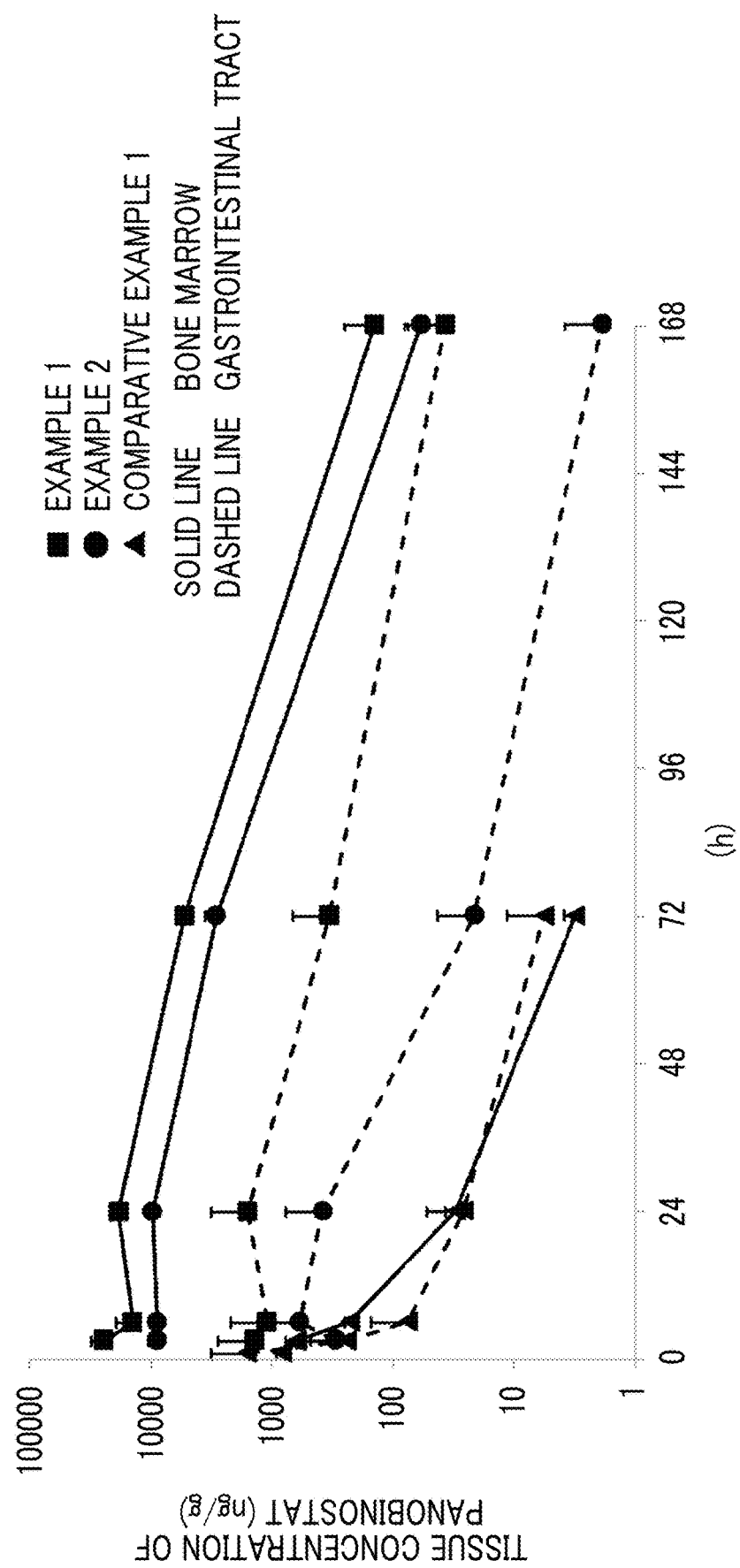
FIG. 3 shows the measurement results of a tissue concentration of panobinostat after the administration of the panobinostat-containing lipid particle or the panobinostat solution.

The mice to which the panobinostat-containing lipid particles prepared in Examples 1, 2, 14, and 19 were administered were dissected at 3, 6, 24, 72, and 168 hours after administration. The mice to which the panobinostat solution prepared in Comparative Example 1 was administered were dissected at 1, 3, 6, 24, and 72 hours after administration, and blood, femoral bone marrow, and gastrointestinal tract (lower ileum) were collected. The blood was centrifuged at 800×g for 10 minutes to recover plasma. The gastrointestinal tract was homogenized by freezing and crushing. With respect to the collected plasma, bone marrow, and gastrointestinal tract, quantification of tissue concentration of panobinostat was carried out using liquid chromatography/mass spectrometry/mass spectrometry (LC/MS/MS). Using the pharmacokinetic analysis software WinNonlin (registered trademark) (available from Certara, L.P.), the area under tissue concentration-time curve (AUC) up to infinite time after single administration was calculated from the transition of the thus-obtained panobinostat concentration in tissues. Further, the bone marrow/gastrointestinal ratio of AUC in tissue was calculated according to Formula 1. The results are shown in FIGS. 2 and 3 and Table 5.

bone marrow/gastrointestinal tract ratio=bone marrow panobinostat AUC/gastrointestinal tract panobinostat AUC=(area under bone marrow concentration-time curve)/(area under gastrointestinal tract concentration-time curve)    Formula 1:

<Measurement of Tissue Concentration of Pemetrexed>

The pemetrexed-containing lipid particles (1.5 mg/kg in terms of a drug amount) prepared in Comparative Example 3 were administered to ICR mice (male, 7 weeks old) from the tail vein.

The mice to which the pemetrexed-containing lipid particles prepared in Comparative Example 3 were administered were dissected at 24, 72, 120, and 168 hours after administration, and blood, femoral bone marrow, and gastrointestinal tract (lower ileum) were collected. The tissue concentration of pemetrexed was quantified in the same manner as in panobinostat, and the AUC and bone marrow/gastrointestinal ratio of AUC in tissues were calculated. The results are shown in Table 5.

TABLE 5

Tissue panobinostat AUC (time × ng/mL) (Comparative Example 1, Examples 1, 2, 14, and 19)
Tissue pemetrexed AUC (time × ng/mL) (Comparative Example 3)

|  | Comparative Example 1 | Comparative Example 3 | Example 1 | Example 2 | Example 14 | Example 19 |
| --- | --- | --- | --- | --- | --- | --- |
| Bone marrow | 5914 | 26479 | 1114988 | 565474 | 253778 | 349117 |
| Gastrointestinal tract | 6241 | 24655 | 86028 | 18051 | 26023 | 18021 |
| Bone marrow/ gastrointestinal tract ratio | 1.0 | 1.1 | 13.0 | 31.3 | 9.8 | 19.4 |

From the above results, the panobinostat-containing lipid particles prepared in Examples 1, 2, 14, and 19 were shown to have a high bone marrow/gastrointestinal tract ratio and satisfactory bone marrow accumulation properties with respect to panobinostat AUC in tissue, in comparison with the panobinostat solution prepared in Comparative Example 1 and the pemetrexed-containing lipid particles prepared in Comparative Example 3.

<Drug Efficacy Test Using Molm-13 Orthotopic Model Mouse>

NOD/SCID mice (male, 8 weeks old) were immunosuppressed with cyclophosphamide (125 mg/kg, intraperitoneal administration for 2 consecutive days) and rabbit anti-asialo GM1 antibody (available from Wako Pure Chemical Industries, Ltd., 0.4 mg, intraperitoneal administration, single administration). $3 \times 10^6$ cells of Molm-13, which is a human leukemia cell line, were transplanted intravenously and engrafted in the bone marrow. From Day 8 after transplantation, administration of the panobinostat-containing lipid particles prepared in Example 1 (8 mg/kg in terms of a drug amount, tail vein administration, single administration), the panobinostat solution prepared in Comparative Example 1 (5 mg/kg, intraperitoneal administration for 8 consecutive days), and the lipid particles without containing panobinostat prepared in Comparative Example 2 (amount of lipid equivalent to 8 mg/kg of the panobinostat-containing lipid particles prepared in Example 1, tail vein administration, single administration) as a negative control was started. In addition, the group not subjected to immunosuppression and transplantation was set as a non-transplantation group. At Day 16 after transplantation (8 days after the start of administration), the mice were dissected and femoral bone marrow was collected. The obtained bone marrow was treated with a hemolysis buffer to remove erythrocytes, and then stained with PerCP-labeled anti-human CD45 antibody and 4,6-diamidino-2-phenylindole (DAPI). In addition, PerCP indicates peridinin chlorophyll-protein complex. The percentage of leukemia cells (human CD45-positive, DAPI-negative cells) in live bone marrow cells was measured using flow cytometry, and a growth inhibitory activity against leukemia cells in Molm-13 orthotopic model mice was compared. The measurement results are shown in FIG. 4.

Figure 4:
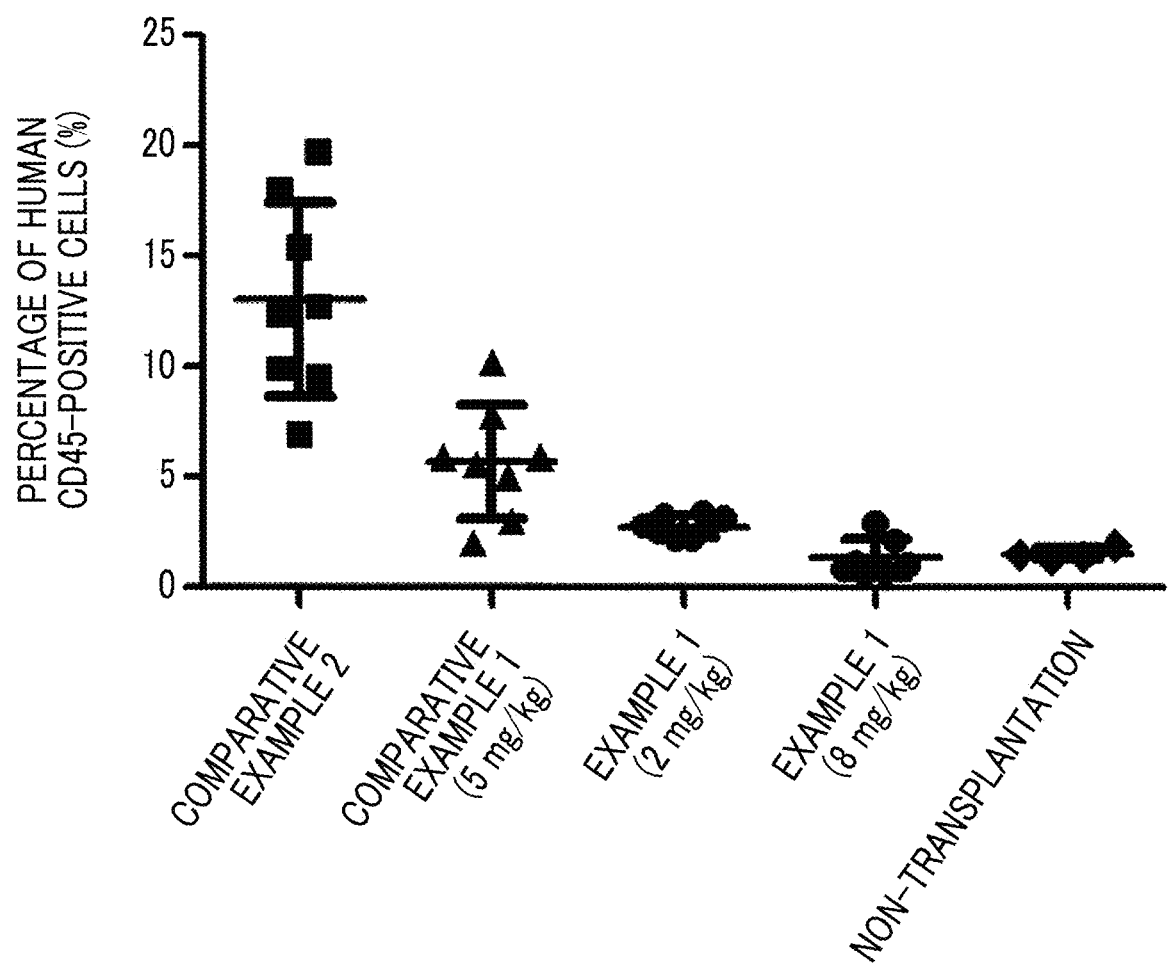
FIG. 4 shows the measurement results of growth inhibitory activity against leukemia cells in a Molm-13 orthotopic model mouse.

From the results shown in FIG. 4, it was found that, as compared with the panobinostat solution prepared in Comparative Example 1 and the lipid particles without containing panobinostat prepared in Comparative Example 2, the panobinostat-containing lipid particles prepared in Example 1 exhibit high growth inhibitory activity against leukemia cells, the effect of which is dose-dependent.

<Analysis of Number of Macrophages in Bone Marrow and Amount of Lipid Particles in Cells>

Figure 5:
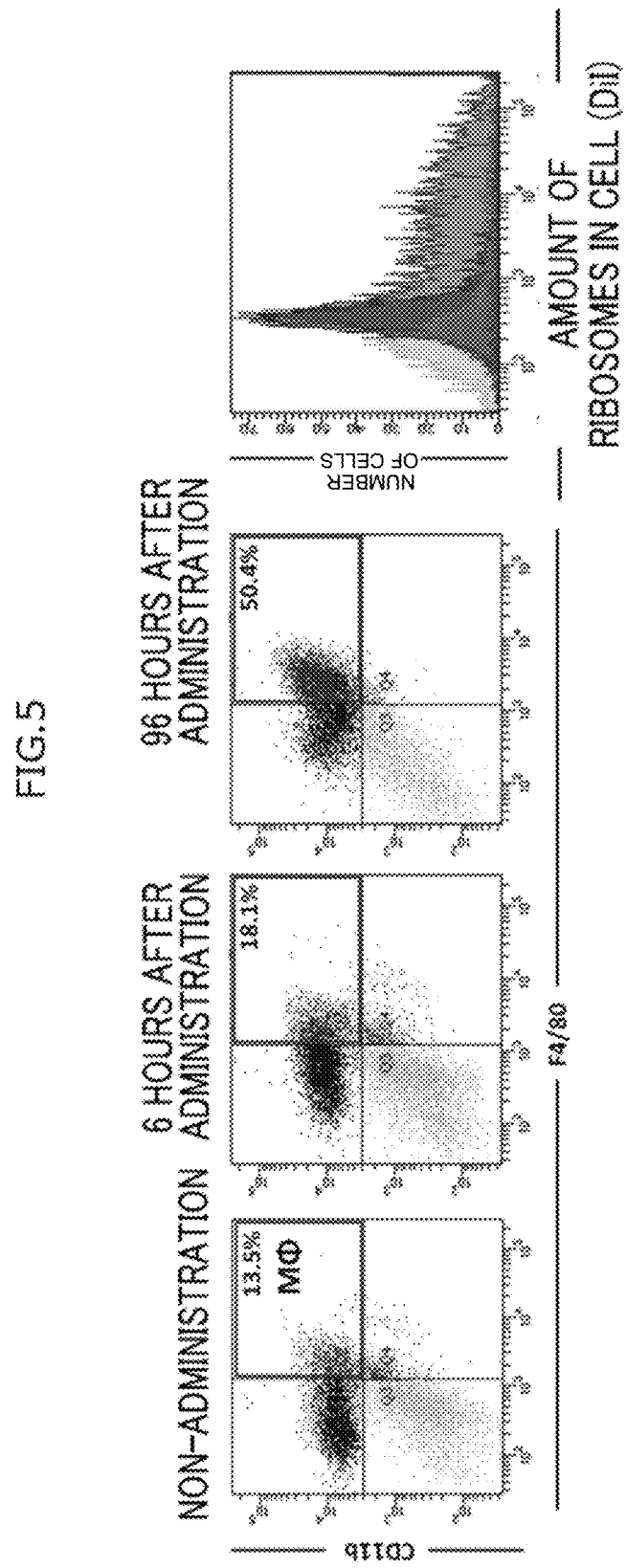
FIG. 5 shows the results of analyzing the number of macrophages in bone marrow and the amount of lipid particles in cells.

The panobinostat-containing lipid particles prepared in Example 2 and labeled with DiI were administered with 6 mg/kg of panobinostat in terms of a drug amount to ICR mice (male, 7 weeks old) from the tail vein. After non-administration, 6 hours after administration, and 96 hours after administration, the mice were dissected and femoral bone marrow was collected. The obtained bone marrow was treated with a hemolysis buffer to remove erythrocytes, and then stained with Alexa fluor (registered trademark) 647-labeled anti-mouse F4/80 antibody, FITC-labeled anti-mouse CD11b antibody, and DAPI. FITC indicates fluorescein isothiocyanate. The percentage of macrophages (mouse F4/80-positive, mouse CD11-positive, DAPI-negative cells) in live bone marrow cells was measured using flow cytometry. Further, for the sample 96 hours after administration, the amount of lipid particles taken into cells was analyzed using the intracellular fluorescence intensity of DiI as an index. The analysis results are shown in FIG. 5. In FIG. 5, Mφ indicates macrophages.

From the results shown in FIG. 5, it was found that the number of macrophages in the bone marrow increases with the passage of time after administration of the panobinostat-containing lipid particles prepared in Example 2, and the panobinostat-containing lipid particles are taken up by the increased macrophages.

<Analysis of Bone Marrow Cytokine Expression>

Panobinostat-containing lipid particles prepared in Example 2 (4 mg/kg in terms of a drug amount, tail vein administration, single administration) and the panobinostat solution prepared in Comparative Example 1 (5 mg/kg, intraperitoneal administration, single administration) were administered to ICR mice (male, 7 weeks old), and 72 hours after administration, the mice were dissected to collect femoral bone marrow. In addition, femoral bone marrow was obtained also for non-administered mice as a negative control. After addition of 3 times the bone marrow weight of PBS, the supernatant was recovered by centrifugation at 300×g for 5 minutes. The protein concentration in the obtained bone marrow supernatant was measured by a BCA method (bicinchoninic acid method), and each sample was diluted to a protein concentration of 8 mg/mL. The cytokine concentration in each sample was quantified using a Bio-Plex mouse cytokine G123-Plex panel and a Bio-Plex 200 system (available from Bio-Rad Laboratories, Inc.). Changes in the relative expression level in a case where the average value of the cytokine expression level at the time of non-administration was taken to be 1 were shown. The analysis results are shown in FIG. 6.

Figure 6:
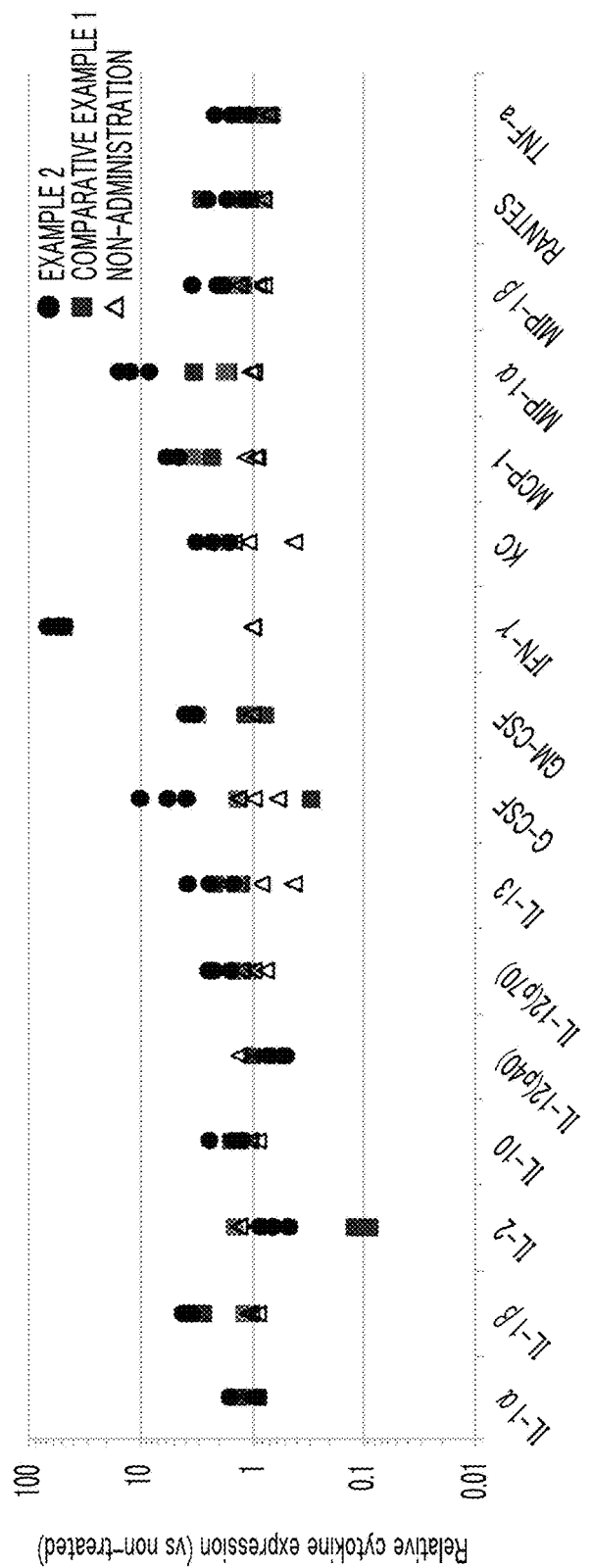
FIG. 6 shows the results of analyzing the expression of cytokines in bone marrow.

In FIG. 6, IL indicates an interleukin, G-CSF indicates a granulocyte colony stimulating factor, GM-CSF indicates a granulocyte/monocyte colony stimulating factor, IFN indicates an interferon, KC indicates a keratinocyte chemoattractant, MCP indicates a monocyte chemotactic protein, MIP indicates a macrophage inflammatory protein, RANTES indicates regulated on activation normal T expressed and secreted, and TNF indicates a tumor necrosis factor.

From the results shown in FIG. 6, in a case where the panobinostat-containing lipid particles prepared in Example 2 or the panobinostat solution prepared in Comparative Example 1 was administered, a tendency was observed that the expression of cytokines increases as compared to a case of non-administration. In the panobinostat-containing lipid particles prepared in Example 2, the expression of cytokines was further enhanced. An increase in cytokine expression is considered as a factor that macrophages accumulate in the bone marrow.

What is claimed is:

1. A liposome composition comprising:
   panobinostat or a salt thereof, and liposomes;
   wherein an area ratio represented by Formula 1 up to infinite time after single administration of a liposome composition of 4 mg/kg as a panobinostat amount to a tail vein of a mouse is 5 or more:
   Formula 1: (area under bone marrow concentration-time curve)/(area under gastrointestinal tract concentration-time curve).

2. The liposome composition according to claim 1, wherein the liposome has an average particle size of 50 nm to 500 nm.

3. The liposome composition according to claim 1, wherein the panobinostat or the salt thereof is encapsulated in the liposome by a remote loading method.

4. The liposome composition according to claim 1, wherein the liposome contains a phospholipid and cholesterol.

5. The liposome composition according to claim 4, which contains a phospholipid having a glycerol skeleton, as the phospholipid.

6. The liposome composition according to claim 5, wherein the phospholipid having a glycerol skeleton is phosphatidylcholine.

7. The liposome composition according to claim 4, which contains a sphingophospholipid as the phospholipid.

8. The liposome composition according to claim 7, wherein the sphingophospholipid is sphingomyelin.

9. The liposome composition according to claim 4, wherein the phospholipid contains a fatty acid residue having 20 or more carbon atoms.

10. The liposome composition according to claim 4, wherein the liposome further contains a polyethylene glycol lipid.

11. The liposome composition according to claim 10, wherein a percentage of the polyethylene glycol lipid in total lipids constituting the liposome is 5 mol % or less.

12. The liposome composition according to claim 4, wherein the liposome is substantially free of a polyethylene glycol lipid.

13. The liposome composition according to claim 4, wherein the liposome contains an anionic lipid.

14. A pharmaceutical composition comprising:
   the liposome composition according to claim 1.

15. The pharmaceutical composition according to claim 14, which is an anticancer agent.

* * * * *